United States Patent
Forsell

(10) Patent No.: US 7,988,616 B2
(45) Date of Patent: Aug. 2, 2011

(54) IMPLANTABLE PUMP FOR OPERATION OF HYDRAULIC IMPLANT

(75) Inventor: Peter Forsell, Zug (CH)

(73) Assignee: Potencia Medical AG, Baar (CH)

( * ) Notice: Subject to any disclaimer, the term of this patent is extended or adjusted under 35 U.S.C. 154(b) by 1377 days.

(21) Appl. No.: 10/530,015

(22) PCT Filed: Oct. 1, 2003

(86) PCT No.: PCT/SE03/01531
§ 371 (c)(1),
(2), (4) Date: Sep. 26, 2005

(87) PCT Pub. No.: WO2004/030746
PCT Pub. Date: Apr. 15, 2004

(65) Prior Publication Data
US 2006/0127246 A1    Jun. 15, 2006

Related U.S. Application Data

(63) Continuation-in-part of application No. 10/260,533, filed on Oct. 1, 2002, now abandoned.

(51) Int. Cl.
*A61F 2/04* (2006.01)
(52) U.S. Cl. .......................................................... 600/31
(58) Field of Classification Search .............. 600/38–41, 600/37, 28–31; 417/234, 412, 437, 474; 604/93, 131, 132, 86
See application file for complete search history.

(56) References Cited

U.S. PATENT DOCUMENTS

| 4,190,040 A * | 2/1980 | Schulte ........................ 128/899 |
| 4,342,308 A * | 8/1982 | Trick ............................ 600/40 |
| 4,408,597 A | 10/1983 | Tenney, Jr. |
| 4,559,931 A * | 12/1985 | Fischell ........................ 600/40 |
| 4,634,443 A | 1/1987 | Haber |
| 4,773,403 A | 9/1988 | Daly |
| 5,078,676 A | 1/1992 | Bailly |
| 5,435,230 A * | 7/1995 | Phillips ......................... 92/91 |

(Continued)

FOREIGN PATENT DOCUMENTS

EP    0252258 A1    1/1988

(Continued)

OTHER PUBLICATIONS

International Search Report of PCT/SE03/01531 mailed Dec. 9, 2003.

(Continued)

*Primary Examiner* — Samuel G Gilbert
(74) *Attorney, Agent, or Firm* — Nixon & Vanderhye P.C.

(57) ABSTRACT

An implantable pump for pumping fluid to or from a hydraulic surgical implant inside a human's or an animal's body comprises a wall forming a chamber for the fluid, the wall including a base plate and a membrane, which is displaceable relative to the base plate to change the volume of the chamber to pump the fluid between the chamber and the surgical implant. The membrane is penetrable by an injection needle to add hydraulic fluid to or withdraw hydraulic fluid from the chamber, in order to calibrate the amount of fluid, and the membrane is self-sealing to seal the hole which is formed in the membrane by the penetrating injection needle. The implant typically is a hydraulic constriction device, which can be designed for treating reflux disease, urinary incontinence, impotence, anal incontinence or obesity.

13 Claims, 4 Drawing Sheets

U.S. PATENT DOCUMENTS

Figure 1:
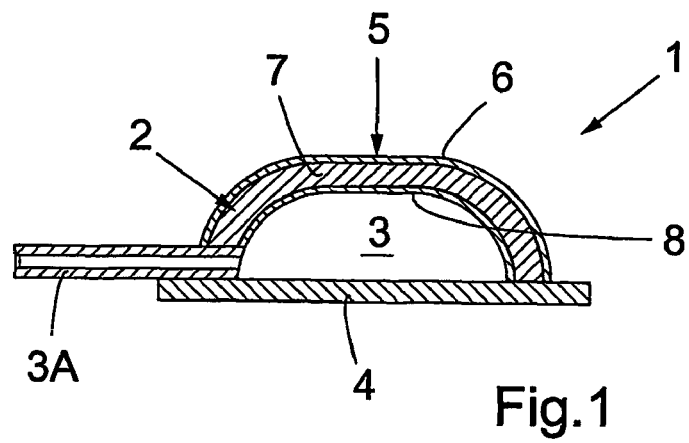

| | | | |
|---|---|---|---|
| 5,562,598 A * | 10/1996 | Whalen et al. | 600/29 |
| 5,704,915 A | 1/1998 | Melsky et al. | |
| 5,836,935 A | 11/1998 | Ashton et al. | |
| 6,074,341 A | 6/2000 | Anderson et al. | |

FOREIGN PATENT DOCUMENTS

| | | |
|---|---|---|
| EP | 0532162 A1 | 3/1993 |
| JP | 58-190437 | 11/1983 |
| JP | 62-8752 | 1/1987 |
| JP | 63-18177 | 7/1988 |
| JP | 1-305945 | 12/1989 |
| JP | 2-211170 | 8/1990 |
| JP | 3-63047 | 3/1991 |
| JP | 3-158154 | 7/1991 |
| JP | 2002-517277 | 6/2002 |
| WO | 99/63907 | 12/1999 |
| WO | 01/47435 A2 | 2/2001 |
| WO | 0147434 A2 | 7/2001 |

OTHER PUBLICATIONS

Office Action in corresponding Japanese Appl. No. JP 2004-541382, dated May 12, 2009 and English translation thereof.

Decision of Final Rejection in corresponding Japanese Application No. 2004-541382, dated Aug. 23, 2010, mail date Sep. 7, 2010 with English translation.

Notice of Preliminary Rejection in corresponding Korean Application No. 2005-7005480, issued Sep. 28, 2010 with English translation.

Office Action in corresponding Canadian Application No. 2,498,042, issued Feb. 2, 2010.

* cited by examiner

IMPLANTABLE PUMP FOR OPERATION OF HYDRAULIC IMPLANT

This application is the US national phase of International Application PCT/SE03/01531 filed Oct. 1, 2003, which designated the U.S. and which is a continuation-in-part of U.S. Ser. No. 10/260,533, filed Oct. 1, 2002 now abandoned, the entire contents of each of which are hereby incorporated by reference herein.

The present invention relates to an implantable pump for pumping hydraulic fluid to or from a hydraulically operable surgical implant inside a human's or an animal's body. The pump comprises a wall forming a chamber for the hydraulic fluid, the wall including a first wall portion and a second wall portion, which is displaceable relative to the first wall portion to change the volume of the chamber to pump the hydraulic fluid between the chamber and the surgical implant.

Such an implantable pump is disclosed in U.S. Pat. No. 4,982,731 and is hydraulically connected to an inflatable cuff forming an annular band around the penis of an impotent patient. This prior art pump includes a squeezable relatively large reservoir in the form of an elastomeric bladder for hydraulic fluid. The reservoir is implanted in the patient's scrotum, so that the patient is enabled to enhance erection by finger-depressing the squeezable reservoir a number of times to cause the cuff to restrict venous drainage.

An object of the present invention is to provide an implantable pump, which is thinner and smaller than that of the prior art, and, therefore, more easily implanted subcutaneously. Another object of the present invention is to provide an implantable pump, which is more versatile than that of the prior art. A further object of the present invention is to provide an implantable pump that is easy to calibrate.

Accordingly, in accordance with a first aspect of the present invention, there is provided a new implantable pump of the type presented initially characterized in that the second wall portion includes a displaceable membrane that is penetrable by an injection needle to add hydraulic fluid to or withdraw hydraulic fluid from the chamber, and that the membrane is self-sealing to seal the hole which is formed in the membrane by the penetrating injection needle. As a result, the amount of hydraulic fluid pumped by the pump can be easily calibrated even when the pump has been subcutaneously implanted in a patient. Thus, the injection needle of a syringe can readily penetrate the patient's skin in front of the membrane and further penetrate the membrane of the pump, so that hydraulic fluid can be added to or removed from the pump chamber from outside the patient's body.

In accordance with a most simple embodiment, the membrane is manually displaceable, i.e. by pushing with a finger the patient's skin in front of the membrane of the subcutaneously implanted pump. In accordance with an alternative the membrane may be magnetically displaceable. Thus, the membrane can be made of a magnetic material or be provided with magnetic elements, and an external permanent magnet or solenoid can be used for repelling and pulling the membrane. In accordance with another alternative, the pump may comprise a motor, which may be remote controlled, adapted to displace the membrane.

Specifically, the membrane is displaceable relative to the first wall portion between a first position, in which the chamber has a first volume, and a second position, in which the chamber has a second volume smaller than the first volume. The membrane preferably is flexible and takes the shape of a semi-sphere, when it is in the first position. Accordingly, when the membrane is displaced to its second position the chamber is substantially emptied and the membrane is in a state of tension.

The implantable pump may further comprise a locking device adapted to releasably lock the membrane in the second position. Thus, the membrane can be displaced from the first position to the second position by manually depressing the membrane. Moreover, the locking device can be adapted to release the membrane from the second position upon pushing the membrane, and the membrane can be adapted to resume its semi-spherical shape in the first position, when it is released from the second position.

In accordance with a preferred embodiment of implantable pump, the membrane includes a first layer and a second layer attached to each other, the first layer having better strength properties than the second layer and the second layer having better sealing properties than the first layer. As a result, the thickness of the membrane can be very small, i.e. about 3 mm. Thus, the pump of the present invention can be designed relatively thin, which facilitates subcutaneous implantation of the pump.

The membrane layers may be made of silicone, wherein the first silicone layer is harder than the second silicone layer. The second silicone layer suitably has a hardness less than 20 Shore. Generally, the second layer is situated between the first layer and the chamber of the injection port. Alternatively, the membrane may comprise a third layer harder than the second layer, wherein the third layer is situated between the second layer and the chamber. The silicone membrane is mounted under tension, which makes it possible to inject a specific type of hypodermic needle into the fluid chamber of the pump, without causing leakage through the membrane after the needle has been removed from the membrane. This type of hypodermic needle has a lateral opening and does not cut out any remaining hole in the silicone membrane. The needle just moves the silicone material aside.

In accordance with a second aspect of the present invention, there is provided an apparatus for treating a disease, comprising a hydraulically operable surgical implant, and the implantable pump of the invention for pumping hydraulic fluid to or from the surgical implant.

Generally, the surgical implant comprises a hydraulic constriction device for constricting a passageway of an organ of a human or an animal. The constriction device may be used for constricting the stomach of an obese patient to restrict the patient's food intake, for constricting the esophagus of a patient who suffers from reflux disease, or for restricting the exit penile blood of an impotent patient. Alternatively, the constriction device may be used as an artificial sphincter in an anal or urinary incontinent patient.

In accordance with an embodiment of the apparatus of the invention, the constriction device comprises an inflatable cavity, which is in fluid communication with the chamber of the pump. The cavity is adapted to constrict the passageway when it is inflated and to release the passageway when it is deflated.

In accordance with another embodiment of the apparatus of the invention, the constriction device comprises a relatively small first inflatable cavity, which is in fluid communication with the chamber of the pump, and a relatively large second cavity, which is displaceable by the first cavity. The first cavity is adapted to displace the second cavity to constrict the passageway when the first cavity is inflated and to displace the second cavity to release the passageway when the first cavity is deflated. The second cavity may also be inflatable by fluid. In this case, the apparatus suitably comprises an injection port, which is in fluid communication with the second cavity.

As a result, the volume of the second cavity can be calibrated by adding fluid to or withdrawing fluid from the injection port.

Advantageously, the surgical implant and pump of the apparatus are connected to form an operable pump assembly, which is easy to implant in the patient. An operation device may operate the pump assembly and an implantable motor may drive the operation device. The motor and or other energy consuming parts of the pump assembly may be designed to be powered by wireless energy emitted outside the patient's body.

The apparatus suitably comprises an energy transmission device for wireless transmission of energy from outside the patient's body to inside the patient's body for use in connection with the operation of the pump assembly. The energy transmission device transmits energy of a first form and the pump assembly is operable in response to energy of a second form. The apparatus further comprises an energy transforming device implantable in the patient for transforming the energy of the first form wirelessly transmitted by the energy transmission device into the energy of the second form, which is different than the energy of the first form.

The energy transforming device may include at least one element having a positive region and a negative region, wherein the element is capable of creating an energy field between the positive and negative regions when exposed to the energy of the first form transmitted by the energy transmission device, and the energy field produces the energy of the second form. For example, the element may include an electrical junction element capable of inducing an electric field between the positive and negative regions when exposed to the energy of the first form transmitted by the energy transmission device, whereby the energy of the second form comprises electric energy.

The energy transforming device may be adapted to transform the energy of the first form directly or indirectly into the energy of the second form, wherein the motor is powered by the energy of the second form. The pump assembly may be operable to perform a reversible function and the motor may be capable of reversing the function. For example, the control device may be adapted to shift polarity of the energy of the second form to reverse the motor. Preferably, the energy transforming device is adapted to directly power the motor by the transformed energy, as the energy of the second form is being transformed from the energy of the first form.

The wireless energy of the first form may include sound waves and the energy of the second form may include electric energy.

In accordance with an embodiment of the invention, the apparatus includes an energy storage device implantable in the patient for storing the energy of the second form and for supplying energy in connection with the operation of the pump assembly. For example, the energy storage device may include an accumulator, such as at least one capacitor or at least one rechargeable battery, or a combination of at least one capacitor and at least one rechargeable battery.

In accordance with another embodiment of the invention, the apparatus includes a source of energy implantable in the patient for supplying energy for the operation of the pump assembly, and a switch operable by the energy of the second form supplied by the energy transforming device to switch from an off mode, in which the source of energy is not in use, to an on mode, in which the source of energy supplies energy for the operation of the pump assembly.

The apparatus may include an implantable stabiliser for stabilising the energy of the second form. Where the energy of the second form includes electric current, the stabiliser includes at least one capacitor.

The apparatus may include implantable electrical components, which may be at least one voltage level guard.

Preferably, the energy transmission device is adapted to transmit wireless energy for direct use in connection with the operation of the pump assembly, as the wireless energy is being transmitted. The wireless energy may be in the form of a magnetic field or electromagnetic waves for direct power of the pump assembly. The energy transforming device may directly operate the pump assembly with the energy of the second form in a non-magnetic, non-thermal or non-mechanical manner.

The energy transforming device suitably includes at least one semiconductor type of component. The semiconductor component may include at least one element having a positive region and a negative region, wherein the element is capable of creating an energy field between the positive and negative regions when exposed to the energy of the first form transmitted by the energy transmission device, and the energy field produces the energy of the second form.

The pump assembly may be operable to perform a reversible function and a reversing device may be implantable in the patient to reverse the function performed by the pump assembly. The control device suitably controls the reversing device to reverse the function performed by the pump assembly. The reversing device may include hydraulic means including a for shifting the flow direction of a liquid flow in the hydraulic means. Alternatively, the reversing device may include a mechanical reversing device, such as a switch.

Preferably, the energy transmission device transmits energy by at least one wireless wave signal, such as an electromagnetic wave signal including one of an infrared light signal, a visible light signal, an ultra violet light signal, a laser signal, a micro wave signal, a radio wave signal, an x-ray radiation signal, and a gamma radiation signal. Alternatively, the wave signal may include a sound or ultrasound wave signal. Any one of these signal types may include a digital or analog signal, or a combination of a digital and analog signal.

The energy of the first form transmitted by the energy transmission device may include an electric, an electromagnetic or a magnetic field, or a combination thereof, which may be transmitted in pulses or digital pulses, or a combination of pulses and digital pulses by the energy transmission device. The energy transforming device suitably transforms the energy of the first form into a direct current or pulsating direct current, or a combination of a direct current and pulsating direct current. Alternatively, the energy transforming device may transform the energy of the first form into an alternating current or a combination of a direct and alternating current.

One of the energy of the first form and the energy of the second form may include magnetic energy, kinetic energy, sound energy, chemical energy, radiant energy, electromagnetic energy, photo energy, nuclear energy or thermal energy. Also, one of the energy of the first form and the energy of the second form may be non-magnetic, non-kinetic, non-chemical, non-sonic, non-nuclear or non-thermal.

Optionally, the energy transmission device may function differently from or similar to the energy transforming device.

The energy transforming device is suitably designed to be implanted subcutaneously or in the abdomen, thorax or cephalic region of the patient. Alternatively, the energy transforming device may be designed to be implanted in an orifice of the patient's body and under the mucosa or intraluminar outside the mucosa of the orifice.

Advantageously, the apparatus of the invention includes a control device, for example a microprocessor, for controlling the pump assembly. Preferably, the control device includes a remote control, conveniently a wireless remote control, for controlling the pump assembly from outside the patient's body. The wireless remote control may include at least one external signal transmitter or transceiver and at least one internal signal receiver or transceiver implantable in the patient. The wireless remote control may be adapted to transmit at least one wireless control signal, which may be a frequency, amplitude or frequency or amplitude modulated signal. The control signal may be an analog or a digital signal, or a combination of an analog and digital signal and the remote control may transmit an electromagnetic carrier wave signal for carrying the digital or analog control signal.

The control signal may be a wave signal including one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The remote control may transmit a carrier signal for carrying the control signal. The carrier signal may include digital, analog or a combination of digital and analog signals. Alternatively, the control signal may include an electric or magnetic field, or a combined electric and magnetic field.

The apparatus may include at least one sensor adapted to be implanted in the patient. The sensor may be adapted to sense at least one physical parameter of the patient and/or at least one functional parameter of a medical implant. Suitably, the control device may control the pump assembly in response to signals from the sensor. The control device may include an implantable internal control unit that directly controls the pump assembly or an external control unit outside the patient's body that controls the pump assembly in response to signals from the sensor.

The apparatus of the invention may include an external data communicator and an implantable internal data communicator communicating with the external data communicator, wherein the internal communicator feeds data related to the pump assembly back to the external data communicator or the external data communicator feeds data to the internal data communicator.

The apparatus of the present invention may be used for any application that requires a small pump injection port system. It may be used for different kinds of implantable hydraulic constriction devices, such as adjustable bands for treating reflux-disease, obesity, urinary incontinence, anal incontinence, and impotence. It may also be used with hydraulic penal implants, as well as with infusion-pumps for drug delivery, etc.

The pump assembly may be used for distributing liquid from one part to another part of a human body.

The apparatus of the invention may also be used in connection with hydraulically controlled implants to distribute liquid within the hydraulic implant or to distribute liquid to and from an implanted liquid reservoir of the implant. Examples of such hydraulically controlled implants are artificial spincters for occluding a body opening for treating anal incontinence, colostomy, ileostomy, jejunostomy, urine incontinence, or hernia in the cardia region. Another example is a hydraulic constriction device for forming a stoma opening in any part of the body for example in the stomach or esophagus of an obese patient to treat obesity.

With regard to anal incontinence, colostomy, ileostomy or jejunostomi, the apparatus of the invention may be used for controlling a hydraulic implant as well as, in a large version of the pump assembly of the apparatus, for pumping fecal matter, which may be discharged through a stomy opening and or through the patient's normal anal canal.

The apparatus of the invention may also be used for treating the vascular system, such as restricting or compressing any part of the vascular system In accordance with a third aspect of the present invention, there is provided a method of operating a hydraulically operable surgical implant implanted in a human or an animal, the method comprising subcutaneously implanting in the human or animal a pump having an injection membrane, which is displaceable to change the volume of a hydraulic fluid chamber in the pump; hydraulically connecting the hydraulic fluid chamber via a conduit to the hydraulically operable surgical implant to form a closed hydraulic fluid distribution system including the fluid chamber, conduit and surgical implant; calibrating the amount of hydraulic fluid in the fluid distribution system by penetrating the patient's skin and the membrane of the implanted pump with an injection needle and adding hydraulic fluid to or withdrawing hydraulic fluid from the fluid chamber; and from time to time, operating the surgical implant by displacing the injection membrane of the subcutaneously implanted pump, so that hydraulic fluid is distributed between the fluid chamber of the pump and the surgical implant.

The method may further comprise operating the surgical implant by manually or magnetically displacing the injection membrane, or, alternatively, by displacing the injection membrane with the aid of a motor.

The present invention also provides a surgical method for treating a patient having a disease, comprising the steps of: insufflating the patient's abdomen with gas; placing at least two laparoscopical trocars in the patient's body; inserting at least one dissecting tool through the trocars and dissecting a region of the patient; implanting a hydraulic surgical implant designed for treating reflux disease, urinary incontinence, impotence, anal incontinence or obesity, in the dissected area by using surgical instruments through the trocars; subcutaneously implanting in the patient a pump having an injection membrane, which is displaceable to change the volume of a hydraulic fluid chamber in the pump; hydraulically connecting the fluid chamber of the pump to the hydraulic surgical implant; calibrating the amount of fluid in the fluid chamber of the pump by penetrating the patient's skin and the membrane of the pump with an injection needle and adding fluid to or withdrawing fluid from the fluid chamber; and from time to time, operating the surgical implant by manually displacing the injection membrane of the subcutaneously implanted pump, so that hydraulic fluid is distributed between the fluid chamber of the pump and the surgical implant.

The above described methods may also be used for treating reflux disease, urine incontinence, impotence, anal incontinence or obesity or the like.

Figure 2:
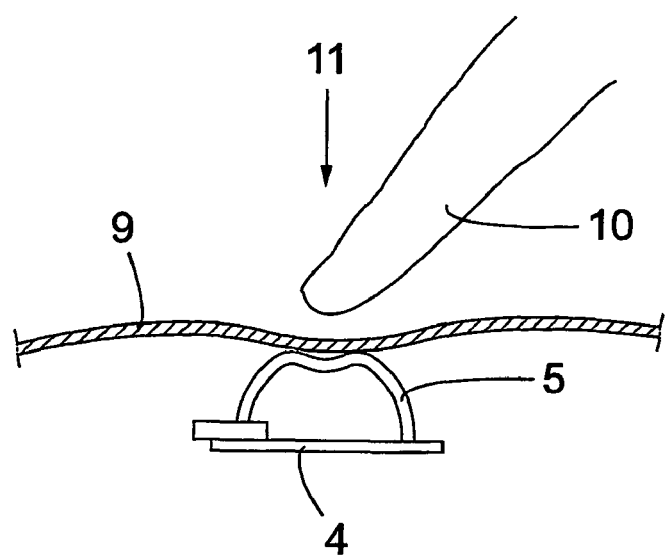
Figure 3:
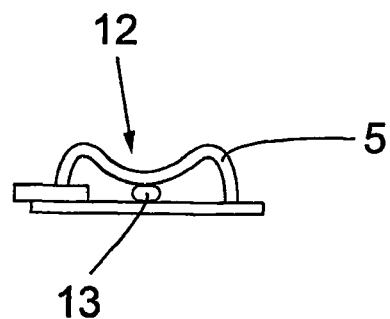
Figure 4:
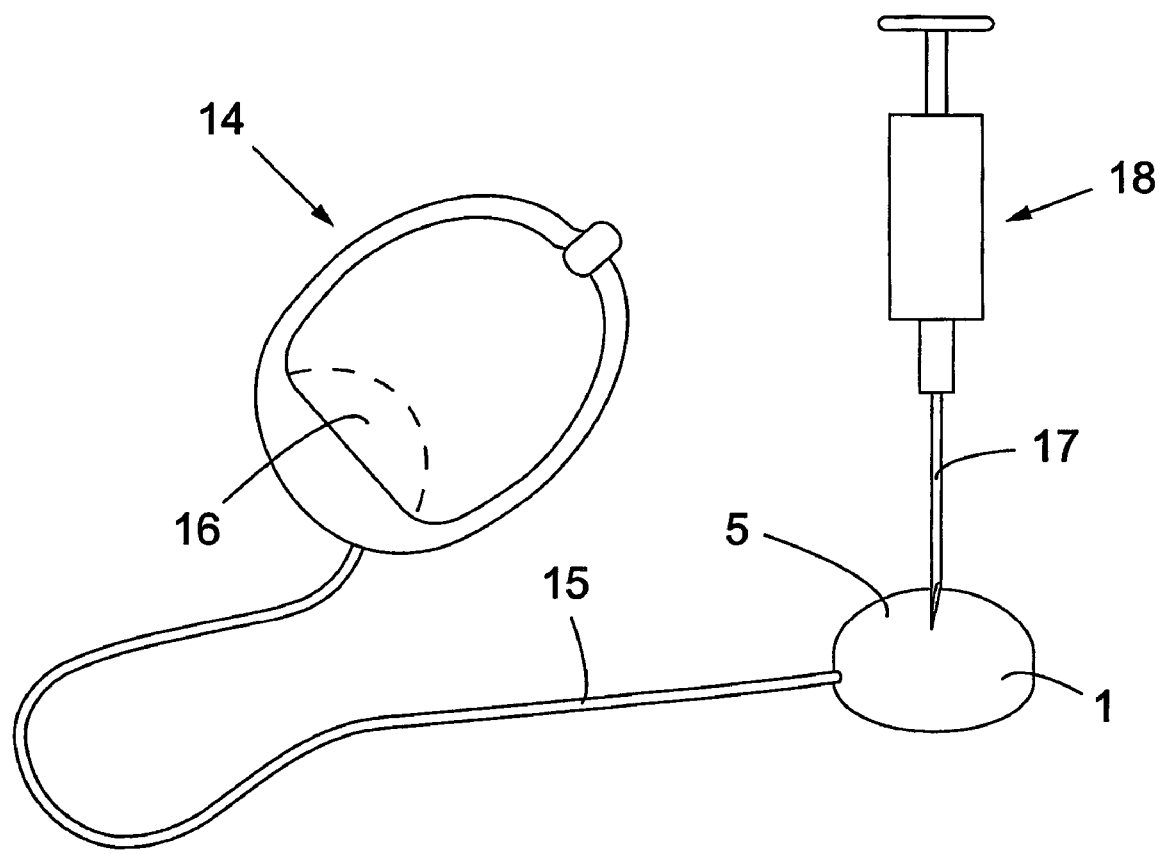
Figure 5:
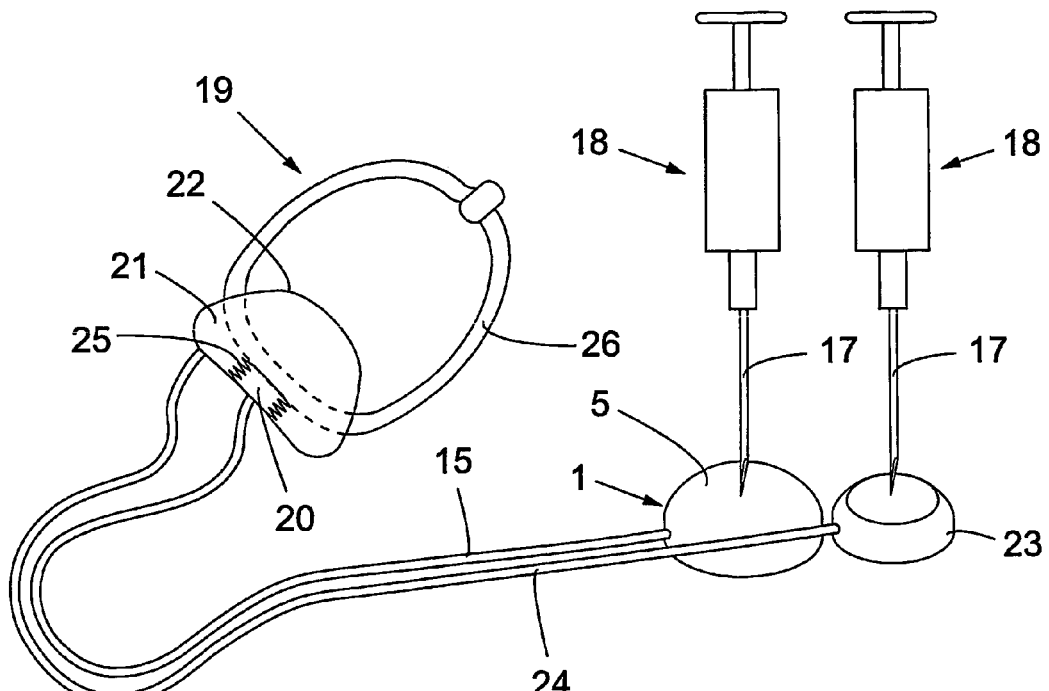
Figure 6:
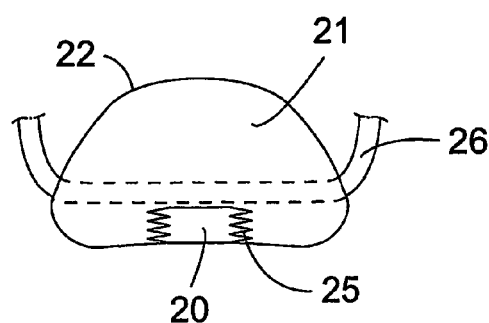
Figure 7:
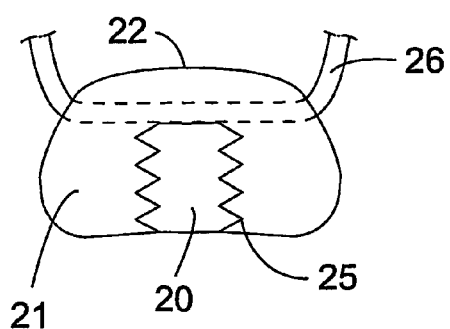
Figure 8:
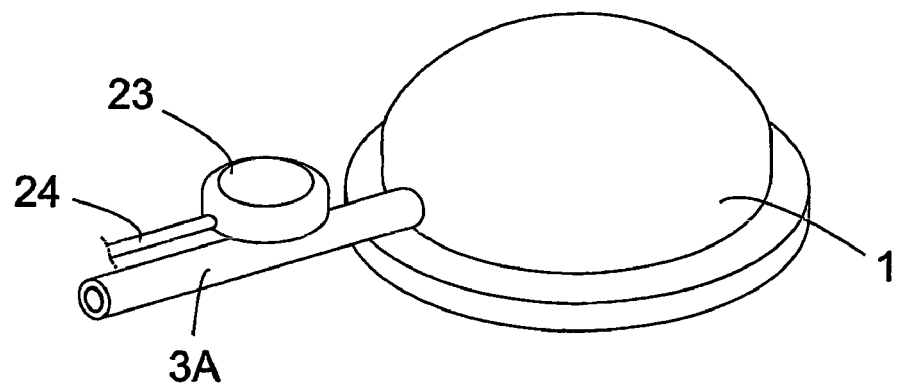
Figure 9:
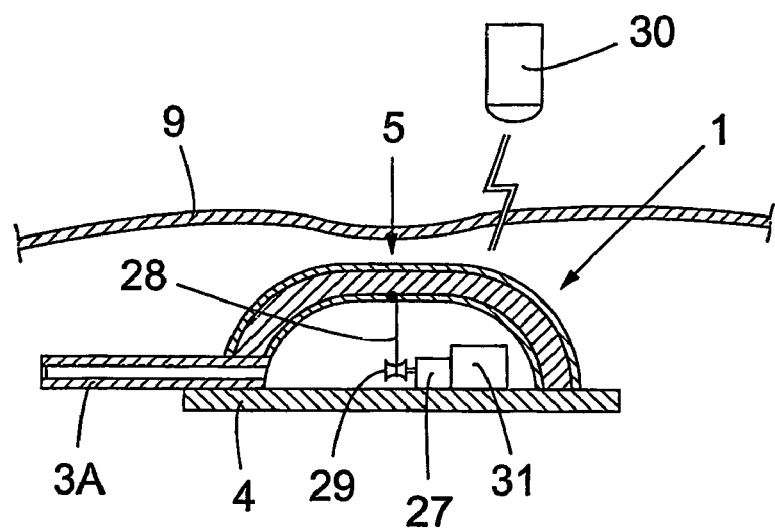

A preferred embodiment of the present invention will now be described by way of example, with reference to the attached drawings, in which FIG. 1 shows an implantable pump according to the present invention, FIG. 2 and 3 illustrate how the pump shown in FIG. 1 is manually operated, FIG. 4 shows an embodiment of an apparatus according to the present invention including the implantable pump shown in FIG. 1, FIG. 5 shows another embodiment of the apparatus of the invention, FIGS. 6 and 7 show details of the embodiment shown in FIG. 5, FIG. 8 shows an alternative design of the embodiment shown in FIG. 5, and FIG. 9 shows another embodiment of the apparatus of the invention with a motor-driven pump.

Referring to the drawing figures, like reference numerals designate identical or corresponding elements throughout the several figures.

FIG. 1 shows an implantable pump 1 according to the present invention including a wall 2 forming a chamber 3 for hydraulic fluid, typically an isotonic salt solution. A nipple 3A for connection to a tube (not shown) for distributing hydraulic fluid from chamber 3 is provided. The wall 2 includes a first wall portion in the form of a rigid base plate 4 and a second wall portion in the form of a relatively thin flexible injection membrane 5, which takes the shape of a semi-sphere and is attached to base plate 4. The injection membrane 5 enables calibration of the pumpable amount of hydraulic fluid by injecting a hypodermic needle through the membrane 5 and adding hydraulic fluid to or withdrawing hydraulic fluid from chamber 3.

Membrane 5 comprises three layers attached to each other: an external first hard layer 6 having preferably a hardness of more than 20 Shore; a central second soft layer 7 having a hardness of less than 20 Shore; and an internal third hard layer 8, having a hardness suitably more than 20 Shore, but preferably about 60 Shore or more. Soft layer 7 has good sealing properties, which means that as soon as an injection needle has been removed from membrane 5 soft layer 7 automatically seals the hole which was created through membrane 5 by the injection needle, when the latter penetrated membrane 5. The strength property of hard layers 6 and 8, and the sealing properties of soft layer 7 enable membrane 5 to be designed particularly thin. Membrane layers 6, 7 and 8 are suitably made of plastic or silicone, preferably of silicone. Suitable silicon materials are manufactured by "Applied Silicone, Inc."

In most applications of the pump of the present invention it is sufficient if membrane 5 comprises only two layers, i.e. the external hard layer 6 and the soft layer 7. Thus, hard layer 7 has better strength properties than soft layer 7, and soft layer 7 has better sealing properties than hard layer 6.

FIGS. 2 and 3 illustrate how pump 1 is manually operated. Since central layer 7 of membrane 5 is very soft, i.e. elastic silicone material of less than 20 Shore, it is possible to design a thin and elastic membrane 5, which allows pumping by hand and yet does not cause leakage when a hypodermic needle penetrates membrane 5. As illustrated in FIG. 2, with pump 1 subcutaneously implanted in a patient, via the patient's skin 9 a finger 10 can push (actuated by one push) membrane 5 in a direction 11 from above. Membrane 5 will then be substantially flattened, such that the surface of membrane 5 that is faced against finger 10 will assume a somewhat concave bowl-shape 12, see FIG. 3. When membrane 5 has been moved to a lowest position a locking device 13 holds it there until it is manually pressed again. When membrane 5 is actuated again, by a second push by finger 10, locking device 13 (which may function similar to the locking mechanism for a ballpoint pen or the like) releases membrane 5, whereby membrane 5 is able to return to its regular convex-shaped state as shown in FIG. 2.

FIG. 4 shows an embodiment of the apparatus of the invention comprising a surgical implant in the form of a hydraulic constriction device 14, the pump 1 of the invention and a tube 15 hydraulically connecting constriction device 14 and pump 1. Constriction device 14 includes an inflatable cavity 16, which is in fluid communication with chamber 3 of pump 5 via tube 15. Thus, the apparatus has a closed hydraulic distribution system including fluid chamber 3, tube 15 and cavity 16.

Constriction device 14 is for restricting a passageway of an organ of a human or an animal. For example, it may be used as an artificial sphincter applied on the urethra of an incontinent patient. The incontinent patient may push membrane 5 of pump 1 to its locked position, in order to inflate cavity 16 to close the urethra and when needed push membrane 5 to release it, so that cavity 16 is deflated and allows the patient to urinate.

The amount of fluid in the fluid distribution system of the apparatus can be calibrated by penetrating membrane 5 of pump 1 with a needle 17 of a syringe 18 and adding hydraulic fluid to or withdrawing hydraulic fluid from chamber 3 of pump 1.

The apparatus shown in FIG. 4 may also be used for treating patients suffering from heartburn and reflux disease, obesity or anal incontinence, or for temporarily restricting the penile exit blood flow of an impotent patient. Thus, in a broad sense, after pump 1 has been subcutaneously implanted in a patient, displaceable injection membrane 5 is used to manually pump hydraulic fluid between fluid chamber 3 and implanted constriction device 14. The total amount of hydraulic fluid in fluid chamber 3, tube 15 and cavity 16 is calibrated by penetrating the patient's skin and membrane 5 with injection needle 17 of syringe 18 to add or withdraw fluid from chamber 5. Membrane 5 is manually displaced from time to time to pump the fluid to or from chamber 3 of pump 1 to operate constriction device 14.

FIG. 5 schematically shows another embodiment of the apparatus of the invention, which is similar to the embodiment shown in FIG. 4, except that the constriction device is designed differently. Thus, the apparatus according to FIG. 5 has a constriction device 19 including a relatively small inflatable cavity 20, which is in fluid communication with chamber 3 of pump 1, and a relatively large cavity 21, which is displaceable by small cavity 20. Small cavity 20 is adapted to displace large cavity 21 to constrict the passageway when small cavity 20 is inflated and to displace large cavity 21 to release the passageway when small cavity 20 is deflated. Thus, a relatively small addition of hydraulic fluid from pump 1 to small cavity 20 causes a relatively large increase in the constriction of the passageway in question.

Large cavity 21 is defined by a big balloon 22, which is connected to an injection port 23 via a tube 24. Adding fluid to or withdrawing fluid from injection port 23 with the aid of syringe 18 calibrates the volume of balloon 22. Small cavity 20 is defined by a small bellow 25, which at one end is attached to an annular frame 26 of constriction device 19 and at the opposite end is attached to balloon 22.

FIGS. 6 and 7 schematically illustrate the operation of constriction device 19. Referring to FIG. 6, when small cavity 20 is deflated bellow 25 pulls balloon 22 inwardly into annular frame 26, so that constriction device 19 constricts the passageway in question. Referring to FIG. 7, when small cavity 20 is inflated bellow 25 pulls balloon 22 out of annular frame 26, so that constriction device 19 releases the passageway.

FIG. 8 shows an alternative design of the apparatus shown in FIG. 5. Thus, in this alternative design injection port 23 is substantially smaller than pump 1 and is attached to nipple 3A of pump 1.

FIG. 9 shows an embodiment of the apparatus of the invention, which differs from the above-described embodiments in that pump 1 is motor driven. Thus, an electric motor 27 for displacing membrane 5 is placed in chamber 3 on base plate

4. A thread 28 is connected between the top portion of membrane 5 and a pulley 29 on a motor axle of motor 27. When motor 27 is activated it winds thread 28 on pulley 29, so that membrane 5 is pulled towards base plate 4. When motor 27 is reversed membrane 5 resumes its semi-spherical shape. Motor 27 is powered by wireless energy transmitted from a control device 30 from outside the patient's skin 9. The wireless energy is transformed into electric energy by a wireless energy transforming device 31 electrically connected to motor 27. Control device 30 controls motor 27.

Although the present invention has been described in terms of particular embodiments, it is not intended that the invention be limited to those embodiments. Modifications of the embodiments within the spirit of the invention will be apparent to those skilled in the art. The scope of the invention is defined by the claims that follow.

The invention claimed is:

1. An implantable pump for pumping hydraulic fluid to or from a hydraulically operable surgical implant inside a human's or an animal's body, the pump comprising:
   a wall forming a chamber for the hydraulic fluid, the wall including a first wall portion and a second wall portion, which is displaceable relative to the first wall portion to change the volume of the chamber to pump the hydraulic fluid between the chamber and the surgical implant, the second wall portion including a displaceable membrane that is penetrable by an injection needle to add hydraulic fluid to, or withdraw hydraulic fluid from the chamber,
   the membrane being self-sealing to seal the hole which is formed in the membrane by the penetrating injection needle,
   the membrane being displaceable relative to the first wall portion between a first position, in which the chamber has a first volume, and a second position, in which the chamber has a second volume smaller than the first volume, and
   a locking device adapted to releasably lock the membrane in the second position,
   the locking device being adapted to lock the membrane in the second position, when the membrane is manually pushed from the first position to the second position,
   the locking device being adapted to release the membrane from the second position upon pushing the membrane, and the membrane is adapted to resume its first position, when it is released from the second position.

2. An implantable pump according to claim 1, wherein the membrane is manually displaceable.

3. An implantable pump according to claim 1, wherein the membrane is flexible and takes the shape of a semi-sphere, when it is in the first position.

4. An implantable pump according to claim 3, wherein the chamber is substantially emptied, when the membrane is in the second position.

5. An implantable pump according to claim 1, wherein the membrane includes a first layer and a second layer attached to each other, the first layer having better strength properties than the second layer and the second layer having better sealing properties than the first layer.

6. An implantable pump according to claim 5, wherein the first layer is harder than the second layer.

7. An implantable pump according to claim 6, wherein the second layer is situated between the first layer and the chamber.

8. An implantable pump according to claim 7, wherein the membrane comprises a third layer harder than the second layer, the third layer being situated between the second layer and the chamber.

9. An implantable pump according to claim 5, wherein the second layer is made of silicone having a hardness of less than 20 Shore.

10. Use of an implantable pump according to claim 1, for pumping hydraulic liquid to and from hydraulic implants designed for treating reflux disease, urine incontinence, impotence, anal incontinence or obesity.

11. An implantable pump according to claim 1, wherein the membrane is magnetically displaceable.

12. An implantable pump according to claim 1, wherein the first wall portion is in the form of a rigid base plate.

13. An implantable pump according to claim 1, wherein the displaceable membrane is flexible and displaceable relative to the first wall portion to change the volume of the chamber to pump the hydraulic fluid between the chamber and the surgical implant.

* * * * *